United States Patent
Harmon et al.

(10) Patent No.: US 6,830,556 B2
(45) Date of Patent: Dec. 14, 2004

(54) DEBRIDEMENT EXTENSION PROVIDING IRRIGATION AND MECHANICAL SCRUBBING FOR REMOVAL OF DEAD, DEVITALIZED, OR CONTAMINATED TISSUE FROM A WOUND

(75) Inventors: Kim R. Harmon, Mineral City, OH (US); Timothy A. Donaldson, Massillon, OH (US); Jeff Boggs, Peachtree, GA (US)

(73) Assignee: Zimmer Orthopaedic Surgical Products, Inc., Dover, OH (US)

( * ) Notice: Subject to any disclaimer, the term of this patent is extended or adjusted under 35 U.S.C. 154(b) by 0 days.

(21) Appl. No.: 10/041,119

(22) Filed: Jan. 8, 2002

(65) Prior Publication Data

US 2003/0130613 A1 Jul. 10, 2003

(51) Int. Cl.$^7$ .......................... A61M 1/00; A61M 5/178; A61M 25/00; A61M 5/00; A61B 17/22
(52) U.S. Cl. .............................. 604/35; 604/30; 604/39; 604/266; 604/247; 606/159; 606/160
(58) Field of Search ............................... 604/35–39, 30, 604/266–247, 34, 541, 45, 8, 902, 21–36; 606/159, 180, 41, 76, 104, 72, 73, 160; 600/365; 137/860; 623/23.63, 23.72

(56) References Cited

U.S. PATENT DOCUMENTS

| | | | |
|---|---|---|---|
| 4,445,509 A | * | 5/1984 | Auth .......................... 606/159 |
| 5,154,499 A | | 10/1992 | Atkinson et al. |
| 5,499,970 A | | 3/1996 | Olson |
| 5,542,918 A | | 8/1996 | Atkinson |
| 5,647,852 A | | 7/1997 | Atkinson |
| 6,129,701 A | * | 10/2000 | Cimino ....................... 604/35 |
| 6,371,934 B1 | * | 4/2002 | Jackson et al. ............... 604/35 |

FOREIGN PATENT DOCUMENTS

WO    WO 98/30207    7/1998

OTHER PUBLICATIONS

Brochure—Pulsavac™—Lavage Debridement System, Snyder Labs, A Subsidiary of Zimmer, 1985.

* cited by examiner

*Primary Examiner*—Nicholas D. Lucchesi
*Assistant Examiner*—Roz Maiorino
(74) *Attorney, Agent, or Firm*—Baker & Daniels

(57) ABSTRACT

A debridement extension including a proximal end and a distal end, with the proximal end being adapted for connection to both an irrigation source and a suction source. The debridement extension includes a fitting adjacent the proximal end which includes both an irrigation port and a suction port. An inner cannula and an outer cannula are both attached to the fitting of the debridement extension and are, respectively, in fluid communication with the irrigation port and the suction port. A debridement tip is affixed to the distal end of the debridement extension and is independently in fluid communication with both the irrigation path and the suction path formed by the inner and outer cannulas, respectively. The debridement tip includes a plurality of irrigation apertures in fluid communication with the irrigation path and spaced about the periphery of the irrigation tip as well as a plurality of suction apertures in fluid communication with the suction path and spaced about the periphery of the debridement tip. The inner and outer cannulas of the debridement extension are flexible so that the debridement extension can be readily inserted into a tract wound for debridement thereof. The debridement tip further includes a plurality of external longitudinal flutes.

19 Claims, 1 Drawing Sheet

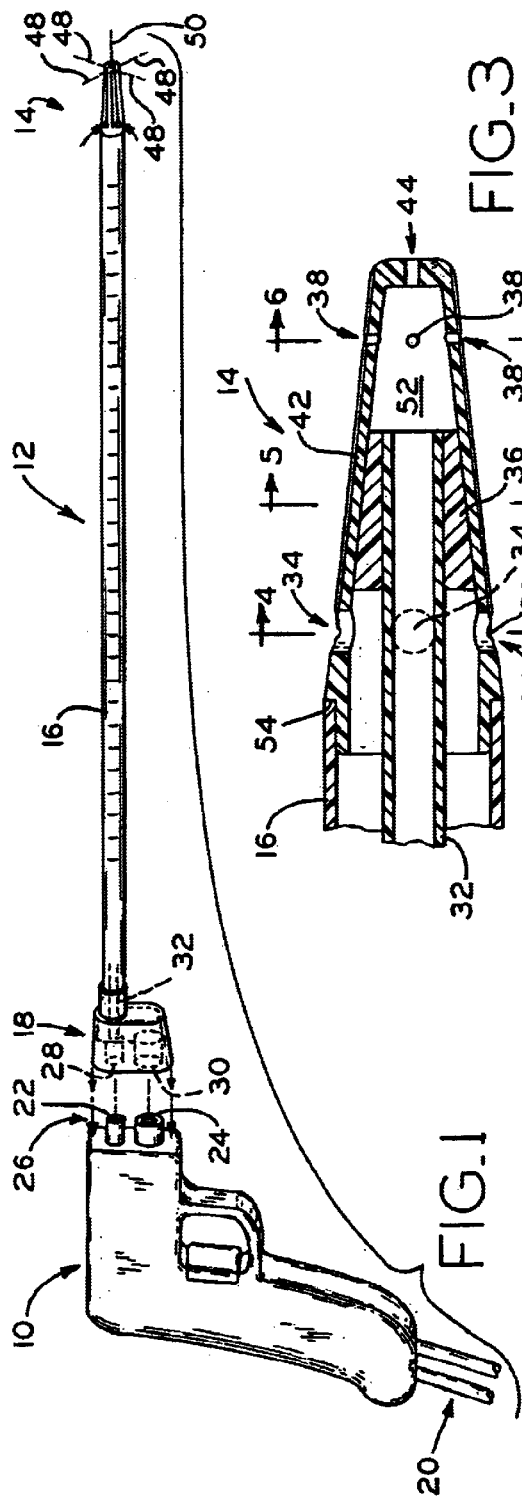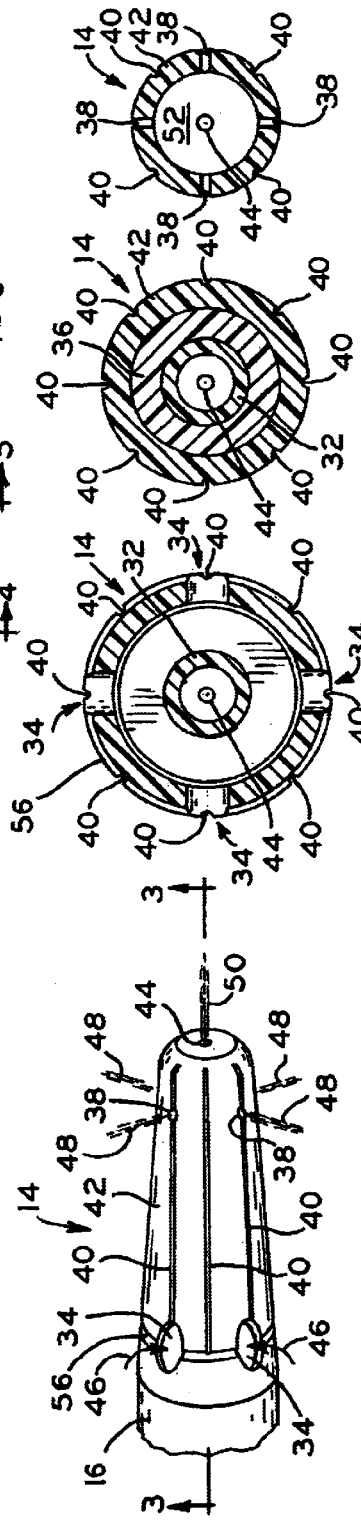

DEBRIDEMENT EXTENSION PROVIDING IRRIGATION AND MECHANICAL SCRUBBING FOR REMOVAL OF DEAD, DEVITALIZED, OR CONTAMINATED TISSUE FROM A WOUND

BACKGROUND OF THE INVENTION

1. Field of the Invention

The present invention relates to a debridement extension for irrigating and suctioning a wound or surgical site. More particularly, the present invention relates to an improved debridement tip for use in a tract wound.

2. Description of the Related Art

Debridement devices are utilized to remove dead, devitalized, or contaminated tissue and other foreign matter from a wound, e.g., a tract wound. A tract wound comprises an externally accessible, elongated wound in the soft tissue of a body. Many times, tract wounds result from a progressively developing infection. For example, when the skin is broken, e.g., by a cut or an external ulcer, and infection develops, the infection can proliferate randomly through the tissue to form a bending, tortuous tunnel, or tract wound. Additionally, tract wounds commonly develop in patients having poor circulation, or a condition in which the patient's ability to overcome infection is decreased, e.g., AIDS. To prevent the infection from spreading and allow the wound to heal, it is important that the dead, devitalized, or contaminated tissue be removed.

What is needed in the art is a debridement tip which allows for the effective removal of infectious material and other debris from the deep regions of a tortuous tract wound. Advantageously, removal of the infectious debris in the deepest region of the wound prevents the infection from proliferating and making the wound deeper.

SUMMARY OF THE INVENTION

The debridement tip of the present invention is affixed to a debridement extension having a proximal end and a distal end, with the proximal end being adapted for connection to both an irrigation source and a suction source. The debridement extension of the current invention includes a fitting adjacent the proximal end thereof. The fitting includes both an irrigation port and a suction port. An inner cannula is attached to the fitting and is in fluid communication with the irrigation port to define an irrigation path from the proximal end of the debridement extension to the distal end thereof. An outer cannula surrounds the inner cannula and is attached to the fitting in fluid communication with the suction port to define a suction path from the proximal end of the debridement extension to the distal end thereof.

A debridement tip is affixed to the distal end of the debridement extension and is independently in fluid communication with both the irrigation path and the suction path formed by the inner and outer cannulas, respectively. The debridement tip includes an irrigation chamber in fluid communication with the irrigation path. A plurality of irrigation apertures are spaced about the periphery of the debridement tip and are in fluid communication with the irrigation chamber, whereby an amount of irrigation fluid in the irrigation chamber traverses the irrigation apertures and exits the debridement tip.

The debridement tip of the present invention further includes a plurality of suction apertures in fluid communication with the suction path. The suction apertures are spaced about the periphery of the debridement tip and allow for the removal of infectious material and other debris dislodged, e.g., by the irrigation stream exiting the irrigation apertures. The debridement extension is flexible so that it is operable to traverse the tortuous path of a tract wound.

In one embodiment of the present invention, the debridement tip is tapered from a proximal end thereof to a distal end thereof. In a further embodiment of the present invention, the irrigation apertures in the debridement tip are more distally located on the debridement tip than the suction apertures. In another alternative embodiment of the present invention, the debridement tip includes a plurality of external longitudinal flutes. Each longitudinal flute can, e.g., span one of the plurality of irrigation apertures and one of the plurality of suction apertures, or span one of the plurality of irrigation apertures and the distal end of the debridement tip. Both the irrigation apertures and the suction apertures can be, e.g., evenly spaced about the periphery of the debridement tip. In one exemplary embodiment, the irrigation apertures and suction apertures are both spaced about the periphery of the debridement tip in ninety degree intervals.

The multiple irrigation apertures of the debridement tip of the current invention advantageously facilitate application of an irrigation fluid stream to the entire surface area of the wound.

Similarly, the multiple suction apertures of the debridement tip of the current invention advantageously facilitate removal of irrigation fluid and dislodged debris from the wound.

The flutes of the debridement tip of the present invention advantageously provide a fluid path from the distal end of the debridement tip to the suction ports and further advantageously provide a texture to the debridement tip of the present invention to facilitate removal of dead, devitalized, or contaminated tissue from a wound.

A BRIEF DESCRIPTION OF THE DRAWINGS

The above-mentioned and other features and objects of this invention, and the manner of obtaining them, will become more apparent and the invention itself will be better understood by reference to the following description of an embodiment of the invention taken in conjunction with the accompanying drawings, wherein:

FIG. 1 is a perspective view of a suction and irrigation system in accordance with the present invention;

FIG. 2 is a partial perspective view of a debridement tip in accordance with the present invention;

FIG. 3 is a sectional view illustrating the connection of the debridement tip to both the inner and outer cannulas of the debridement extension of the present invention; and FIGS. 4–6 are sectional views of a debridement tip in accordance with the present invention.

Corresponding reference characters indicate corresponding parts throughout the several views. Although the drawings represent an exemplary embodiment of the present invention, the drawings are not necessarily to scale and certain features may be exaggerated to better illustrate and explain the invention. The exemplification set out herein illustrates an exemplary embodiment of the invention only and such exemplification is not to be construed as limiting the scope of the invention in any manner.

DETAILED DESCRIPTION OF THE INVENTION

Referring to FIG. 1, debridement extension 12 is adapted for connection to handpiece 10 having suction and irrigation tubing 20 operably connected thereto. Suction and irrigation handpiece 10 operably connects debridement extension 12 (via suction and irrigation tubing 20) to a source of irrigation fluid (not shown) as well as to a source of suction (not shown), as is conventional in the art. Outer cannula 16 of debridement extension 12 is flexible, whereby debridement extension 12 may be fully inserted into a tract wound for debridement along the entire length of the tract wound.

As illustrated in FIG. 1, debridement extension 12 includes fitting 18 operable to connect debridement extension 12 to suction and irrigation handpiece 10. Fitting 18 includes irrigation port 28 and suction port 30 for connection to irrigation port 22 and suction port 24, respectively, on suction and irrigation handpiece 10. As illustrated in FIG. 1, inner cannula 32 of debridement extension 12 is directly fluidly connected to irrigation port 28 to form an irrigation path from irrigation port 28 to debridement tip 14. Similarly, outer cannula 16 is fluidly connected to suction port 30 to form a suction path from suction port 30 to debridement tip 14. As illustrated in FIG. 1, debridement tip 14 is connected to the distal end of debridement extension 12.

As illustrated in FIG. 3, inner cannula 32 terminates in irrigation chamber 52, so that irrigation fluid carried by inner cannula 32 is collected in irrigation chamber 2. As illustrated in FIGS. 2, 3, and 6, debridement tip 14 includes a plurality of irrigation apertures 38 in fluid communication with irrigation chamber 52 and spaced about the periphery of debridement tip 14. In this way, irrigation fluid is carried by inner cannula 32 to irrigation chamber 52 and out of debridement tip 14 through irrigation apertures 38. In one exemplary embodiment, irrigation apertures 38 are spaced about debridement tip 14 in ninety degree intervals. The debridement tip of the current invention may further include axial irrigation aperture 44 positioned on the distal end of debridement tip 14 and in fluid communication with irrigation chamber 52. Axial irrigation aperture 44 is utilized to produce axial irrigation stream 50, as illustrated in FIG. 2, for further wound irrigation As illustrated in FIGS. 2, 3, and 4, debridement tip 14 includes a plurality of suction apertures 34 spaced about the periphery thereof. As illustrated in FIG. 3, the distal end of outer cannula 16 terminates at shoulder 54 of debridement tip 14. Debridement tip 14 is secured to the distal end of outer cannula 16 whereby the suction path formed in outer cannula 16 is in fluid communication with suction apertures 34. As illustrated in FIG. 3, connector 36 is interposed between inner cannula 32 and debridement tip 14 so that the suction path created in outer cannula 16 is out of fluid communication with the irrigation path formed by inner cannula 32.

As illustrated in FIG. 2, radial irrigation streams 48 project outwardly from irrigation apertures 38 to irrigate a wound, e.g., a tract wound. As the wound is irrigated, irrigation fluid and debris are pulled through suction apertures 34 and into the suction path created by outer cannula 16. The path of irrigation fluid and debris into suction apertures 34 and thereafter outer cannula 16 is generally illustrated at 46 in FIG. 2.

As illustrated, e.g., in FIG. 2, debridement tip 14 includes flutes 40 connecting suction apertures 34 and irrigation apertures 38. FIG. 2 illustrates flutes 40 extending from suction apertures 34 to the distal end of debridement tip 14, i.e., the end of debridement tip 14 having axial irrigation aperture 44 formed therein. In an alternative embodiment of the current invention, flutes 40 will span suction apertures 34 and irrigation apertures 38. As illustrated, e.g., in FIGS. 2 and 4, annular channel 56 connects suction apertures 34 and flutes 40. Flutes 40 provide a path for irrigation fluid and debris to enter suction apertures 34. Furthermore, flutes 40 provide a texture to effect a scrubbing action when the tip is maneuvered in the wound as further described below.

Debridement extension 12 may be rotated in combination with axial displacement thereof to facilitate placing debridement tip 14 into the deepest portion of the track wound to be debrided. During rotation of debridement extension 12, outer surface 42 of debridement tip 14 will contact the inner surface of the tract wound being debrided, which will facilitate removal of dead, devitalized, or contaminated tissue from the wound. Mechanical removal of wound debris by rotation of debridement tip 14 is further facilitated by flutes 40 in debridement tip 14. As debridement extension 12 is rotated, wound debris will come into contact with, and be dislodged by flutes 40. In this way, dead, devitalized, or contaminated tissue, and other foreign matter is dislodged by irrigation streams 48, 50, as well as by the placement motion utilized to position debridement tip 14 in the deepest region of the tract wound. As described above, the dislodged debris is collected through suction apertures 34.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present invention as come within known or customary practice in the art to which this invention pertains.

What is claimed is:

1. A debridement extension having a proximal end and a distal end, the proximal end being adapted for connection to an irrigation source and a suction source, the debridement extension comprising:

a fitting adjacent the proximal end, the fitting including an irrigation port and a suction port;

an irrigation cannula attached to said fitting in fluid communication with said irrigation port, said irrigation cannula defining an irrigation path from said proximal end of the debridement extension to the distal end of the debridement extension;

a suction cannula attached to said fitting in fluid communication with said suction port, said suction cannula defining a suction path from the proximal end of the debridement extension to the distal end of the debridement extension; and a debridement tip affixed to said distal end of said debridement extension, wherein said debridement tip is not rotatable relative to said debridement extension, said debridement tip in fluid communication with both said irrigation path and said suction path, said debridement tip having a plurality of irrigation apertures in fluid communication with said irrigation path, said irrigation apertures spaced about the periphery of said debridement tip, whereby an amount of irrigation fluid in said irrigation path traverses said irrigation apertures and exits the debridement tip, said debridement tip including a plurality of external longitudinal flutes.

2. The debridement extension of claim 1, wherein said irrigation cannula comprises an inner cannula and said suction cannula comprises an outer cannula surrounding said inner cannula.

3. The debridement extension of claim 1, wherein said debridement tip further includes a plurality of suction apertures in fluid communication with said suction path and the exterior of said debridement tip.

4. The debridement extension of claim 1, wherein said debridement tip is tapered from a proximal end thereof to a distal end thereof.

5. The debridement extension of claim 1, further comprising an axial irrigation aperture positioned on a distal end of said debridement tip.

6. The debridement extension of claim 1, wherein said plurality of irrigation apertures are spaced about the periphery of said debridement tip in ninety degree intervals.

7. The debridement extension of claim 3, wherein said plurality of suction apertures are spaced about the periphery of said debridement tip in ninety degree intervals.

8. A debridement extension having a proximal end and a distal end, the proximal end being adapted for connection to an irrigation source and a suction source, the debridement extension comprising:
 a fitting adjacent the proximal end, the fitting including an irrigation port and a suction port;
 an irrigation cannula attached to said fitting in fluid communication with said irrigation port, said irrigation cannula defining an irrigation path from said proximal end of the debridement extension to the distal end of the debridement extension;
 a suction cannula attached to said fitting in fluid communication with said suction port, said suction cannula defining a suction path from the proximal end of the debridement extension to the distal end of the debridement extension; and
 a debridement tip affixed to said distal end of said debridement extension, wherein said debridement tip is not rotatable relative to said debridement extension, said debridement tip in fluid communication with both said irrigation path and said suction path, said debridement tip having a plurality of irrigation apertures in fluid communication with said irrigation path, said irrigation apertures spaced about the periphery of said debridement tip, whereby an amount of irrigation fluid in said irrigation path traverses said irrigation apertures and exits the debridement tip, said debridement tip including a plurality of external longitudinal flutes, wherein each of said longitudinal flutes is in fluid communication with at least one of said plurality of suction apertures.

9. A debridement extension having a proximal end and a distal end, the proximal end being adapted for connection to an irrigation source and a suction source, the debridement extension comprising:
 a fitting adjacent the proximal end, the fitting including an irrigation port and a suction port;
 an irrigation cannula attached to said fitting in fluid communication with said irrigation port, said irrigation cannula defining an irrigation path from said proximal end of said debridement extension to said distal end of said debridement extension;
 a suction cannula attached to said fitting in fluid communication with said suction port, said suction cannula defining a suction path from the proximal end of the debridement extension to the distal end of the debridement extension; and
 a debridement tip affixed to said distal end of said debridement extension, wherein said debridement tip is not rotatable relative to said debridement extension, said debridement tip in fluid communication with both said irrigation path and said suction path, said debridement tip having a plurality of suction apertures in fluid communication with said suction path, and the exterior of said debridement tip, said suction apertures spaced about the periphery of said debridement tip, said debridement tip including a plurality of external longitudinal flutes.

10. The debridement extension of claim 9, wherein said irrigation cannula comprises an inner cannula and said suction cannula comprises an outer cannula surrounding said inner cannula.

11. The debridement extension of claim 9, wherein said debridement tip further includes an irrigation chamber in fluid communication with said irrigation path and having a plurality of irrigation apertures in fluid communication with and spaced about the periphery of said irrigation chamber, whereby an amount of irrigation fluid in said irrigation chamber traverses said irrigation apertures and exits the debridement tip.

12. The debridement extension of claim 9, wherein said debridement tip is tapered from a proximal end thereof to a distal end thereof.

13. The debridement extension of claim 9, wherein each of said longitudinal flutes is in fluid communication with at least one of said plurality of suction apertures.

14. A debridement extension having a proximal end and a distal end, the proximal end being adapted for connection to an irrigation source and a suction source, the debridement extension comprising:
 a fitting adjacent the proximal end, the fitting including an irrigation port and a suction port;
 an irrigation cannula attached to said fitting in fluid communication with said irrigation port, said irrigation cannula defining an irrigation path from said proximal end of the debridement extension to the distal end of the debridement extension;
 a suction cannula attached to said fitting in fluid communication with said suction port, said suction cannula defining a suction path from the proximal end of the debridement extension to the distal end of the debridement extension; and
 a debridement tip affixed to said distal end of said debridement extension, wherein said debridement tip is not rotatable relative to said debridement extension, said debridement tip in fluid communication with both said irrigation path and said suction path, said debridement tip having a plurality of irrigation apertures in fluid communication with said irrigation path, whereby an amount of irrigation in said irrigation path traverses said irrigation apertures and exits the debridement tip, said debridement tip further having a plurality of suction apertures in fluid communication with said suction path and the exterior of said debridement tip, said debridement tip having a plurality of external longitudinal flutes.

15. The debridement extension of claim 14, wherein said irrigation cannula comprises an inner cannula and said suction cannula comprises an outer cannula surrounding said inner cannula.

16. A debridement extension having a proximal end and a distal end, the proximal end being adapted for connection to an irrigation source and a suction source, the debridement extension comprising:
 a fitting adjacent the proximal end, the fitting including an irrigation port and a suction port;
 an irrigation cannula attached to said fitting in fluid communication with said irrigation port, said irrigation cannula defining an irrigation path from said proximal end of the debridement extension to the distal end of the debridement extension;

a suction cannula attached to said fitting in fluid communication with said suction port, said suction cannula defining a suction path from the proximal end of the debridement extension to the distal end of the debridement extension; and a debridement tip affixed to said distal end of said debridement extension, wherein said debridement tip is not rotatable relative to said debridement extension, said debridement tip in fluid communication with both said irrigation path and said suction path, said debridement tip having a plurality of irrigation apertures in fluid communication with said irrigation path, said irrigation apertures spaced about the periphery of said debridement tip in ninety degree intervals, whereby an amount of irrigation fluid in said irrigation path traverses said irrigation apertures and exits the debridement tip.

17. The debridement extension of claim 16, wherein said irrigation cannula comprises an inner cannula and said suction cannula comprises an outer cannula surrounding said inner cannula.

18. A debridement extension having a proximal end and a distal end, the proximal end being adapted for connection to an irrigation source and a suction source, the debridement extension comprising:

a fitting adjacent the proximal end, the fitting including an irrigation port and a suction port;

an irrigation cannula attached to said fitting in fluid communication with said irrigation port, said irrigation cannula defining an irrigation path from said proximal end of said debridement extension to said distal end of said debridement extension;

a suction cannula attached to said fitting in fluid communication with said suction port, said suction cannula defining a suction path from the proximal end of the debridement extension to the distal end of the debridement extension; and a debridement tip affixed to said distal end of said debridement extension, wherein said debridement tip is not rotatable relative to said debridement extension, said debridement tip in fluid communication with both said irrigation path and said suction path, said debridement tip having a plurality of suction apertures in fluid communication with said suction path, and the exterior of said debridement tip, said suction apertures spaced about the periphery of said debridement tip in ninety degree intervals.

19. The debridement extension of claim 18, wherein said irrigation cannula comprises an inner cannula and said suction cannula comprises an outer cannula surrounding said inner cannula.

* * * * *